(12) United States Patent
Sazegar et al.

(10) Patent No.: US 12,322,871 B2
(45) Date of Patent: Jun. 3, 2025

(54) METASURFACE ANTENNA WITH INTEGRATED VARACTOR CIRCUITS

(71) Applicant: Kymeta Corporation, Redmond, WA (US)

(72) Inventors: Mohsen Sazegar, Kirkland, WA (US); Hussein Esfahlani, Kirkland, WA (US); Cagdas Varel, Seattle, WA (US); Seyed Mohamad Amin Momeni Hasan Abadi, Redmond, WA (US); Tung Pham, Renton, WA (US); Ryan Stevenson, Woodinville, WA (US); Witold Teller, Kirkland, WA (US); Mohammad Ranjbarnikkhah, Redmond, WA (US); Paul Klassen, Redmond, WA (US)

(73) Assignee: KYMETA CORPORATION, Redmond, WA (US)

( * ) Notice: Subject to any disclaimer, the term of this patent is extended or adjusted under 35 U.S.C. 154(b) by 0 days.

(21) Appl. No.: 17/681,375

(22) Filed: Feb. 25, 2022

(65) Prior Publication Data

US 2022/0278449 A1    Sep. 1, 2022

Related U.S. Application Data

(60) Provisional application No. 63/155,152, filed on Mar. 1, 2021.

(51) Int. Cl.
*H01Q 3/26* (2006.01)
*A61B 17/16* (2006.01)
(Continued)

(52) U.S. Cl.
CPC ....... *H01Q 3/2694* (2013.01); *A61B 17/1615* (2013.01); *H01Q 3/28* (2013.01);
(Continued)

(58) Field of Classification Search
CPC .......... H01Q 1/38; H01Q 3/26; H01Q 3/2694; H01Q 7/06; H01Q 15/00; H01Q 3/28;
(Continued)

(56) References Cited

U.S. PATENT DOCUMENTS 5,987,313 A    11/1999 Lee
11,737,214 B2 *  8/2023 Yeh ........................ H01P 1/2005
                                                                 361/777
(Continued)

FOREIGN PATENT DOCUMENTS

CN    110544815 A  * 12/2019 ............. G04G 21/04
TW    201947815 A    12/2019

OTHER PUBLICATIONS

International Search Report and Written Opinion on the Patentability of Application No. PCT/US2022/018174 Mailed Jun. 16, 2022, 12 pages.
(Continued)

*Primary Examiner* — Ankur Jain
(74) *Attorney, Agent, or Firm* — Womble Bond Dickinson (US) LLP

(57) ABSTRACT

Antennas with integrated varactor circuits are described. The antenna may comprise metasurface antennas. In some embodiments, an antenna comprises an array of antenna elements, wherein each antenna element comprises a iris and a varactor diode integrated on an integrated circuit (IC) chip coupled across a portion of the iris. The antenna can also comprise a plurality of transistors, each transistor coupled to a distinct one of the varactor diodes in the array of antenna elements to provide a tuning voltage to the one varactor diode.

20 Claims, 12 Drawing Sheets

(51) Int. Cl.
  *H01Q 3/28* (2006.01)
  *H04B 1/40* (2015.01)
  *A61B 17/00* (2006.01)
(52) U.S. Cl.
  CPC ...... *H04B 1/40* (2013.01); *A61B 2017/00199* (2013.01); *A61B 2017/00973* (2013.01)
(58) Field of Classification Search
  CPC .... H01Q 13/103; H01Q 15/0086; H04B 1/40; A61B 17/1615; A61B 2017/00199; A61B 2017/00973; A61B 2017/00017; A61B 2017/00225; A61B 17/32002
  See application file for complete search history.

(56) References Cited

U.S. PATENT DOCUMENTS

| | | |
|---|---|---|
| 2008/0290465 A1 | 11/2008 | De Vreede |
| 2010/0090016 A1 | 4/2010 | Jkoyama et al. |
| 2015/0318618 A1 | 11/2015 | Chen et al. |
| 2020/0083605 A1 | 3/2020 | Quarfoth et al. |
| 2021/0050671 A1 | 2/2021 | Stevenson et al. |
| 2021/0234260 A1 | 7/2021 | Thai et al. |

OTHER PUBLICATIONS

International Preliminary Report on Patentability received for PCT Patent Application No. PCT/US22/18174, mailed on Sep. 14, 2023, 8 pages.
Extended European Search Report and Search Opinion received for European Application No. 22763844.2, mailed on Nov. 22, 2024, 12 pages.
Office Action received for Taiwanese Patent Application No. 111107347, mailed on Jan. 13, 2025, 11 pages (4 pages of English Translation and 7 pages of Original Document).

* cited by examiner

Receive a tuning voltage on an IC chip having an varactor diode device (e.g., a single varactor diode, a single varactor diode with a capacitor as a DC block, a pair of varactor diodes) from a transistor (e.g., transistor off the IC chip, transistor on the IC chip)
1101

Adjust the RF characteristics of an antenna element coupled to the IC chip by applying the tuning voltage to the varactor diode
1102

Sense the tuning voltage to be applied to the varactor diode device using a sensor (e.g., voltage sampling circuitry) on the IC chip and sending sensing results (e.g., sensed voltage, indications of a sensed voltage) back to a control unit off the IC chip
1103

Amplify an RF signal received or transmitted through a slot of the antenna element using an amplifier on the IC chip
1104

FIG. 11

METASURFACE ANTENNA WITH INTEGRATED VARACTOR CIRCUITS

RELATED APPLICATION

The present application is a non-provisional application of and claims the benefit of U.S. Provisional Patent Application No. 63/155,142, filed Mar. 1, 2021 and entitled "Metasurface Antenna with Integrated Varactor Circuits", which is incorporated by reference in its entirety.

FIELD OF THE INVENTION

Embodiments of the invention are related to wireless communication; more particularly, embodiments of the invention are related to antennas for wireless communication that utilize varactor diode devices for tuning radio-frequency (RF) radiating antenna elements.

BACKGROUND

Metasurface antennas have recently emerged as a new technology for generating steered, directive beams from a lightweight, low-cost, and planar physical platform. Such metasurface antennas have been recently used in a number of applications, such as, for example, satellite communication.

Metasurface antennas may comprise metamaterial antenna elements that can selectively couple energy from a feed wave to produce beams that may be controlled for use in communication. These antennas are capable of achieving comparable performance to phased array antennas from an inexpensive and easy-to-manufacture hardware platform.

By using simpler elements as compared to phased arrays, the operation of a metasurface is easier and faster. These elements, however, do not exhibit the same level of control as is achievable with phase shifters and amplifiers, common to phased array architectures. Some implementations of metasurface-based antennas do not provide independent control of both the magnitude and phase of each individual element in the array. Such control is desired at times.

SUMMARY

Antennas with integrated varactor circuits are described. The antenna may comprise metasurface antennas. In some embodiments, an antenna comprises an array of antenna elements, wherein each antenna element comprises an iris and a varactor diode integrated on an integrated circuit (IC) chip coupled across a portion of the iris. The antenna can also comprise a plurality of transistors, each transistor coupled to a distinct one of the varactor diodes in the array of antenna elements to provide a tuning voltage to the one varactor diode.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

FIG. 11 is a flow diagram of some embodiments of a process for using a varactor diode device for controlling an antenna element of an antenna.

DETAILED DESCRIPTION

Figure 1:
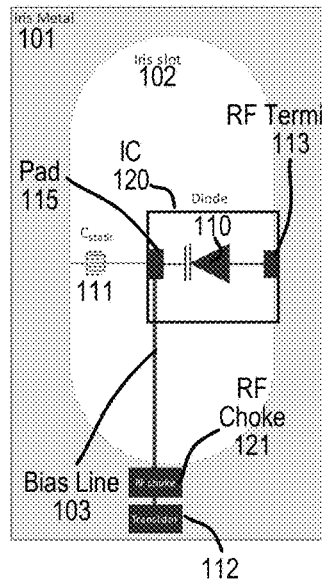
FIG. 1 illustrates one embodiment of a single junction configuration.

Methods and devices are disclosed herein an antenna that includes a varactor diode integrated on an integrated circuit (IC). In some embodiments, a varactor diode described herein can be considered as an integrated circuit (IC) with different levels of integration. In some embodiments, one or more ICs, each with a varactor diode, is integrated in a metasurface antenna having an antenna aperture with antenna elements (e.g., radio-frequency (RF) radiating antenna elements, surface scattering metamaterial antenna elements, etc.). In such case, the IC adjusts the RF characteristics of the antenna element. In some embodiments, the IC can include one or more transistors that act as a switch to apply a tuning voltage on the varactor diode. By including the transistors eliminates the need for external transistor (e.g., matrix drive transistor, direct drive transistor) as the switches are integrated on the IC. Other components such as, for example, resistors, capacitors and inductors can be part of the IC as well.

In some embodiments, a sensor is incorporated into the IC to allow monitoring of the actual voltage at the varactor. This would help troubleshoot antenna performance and improve the in-field optimization of the antenna. In some embodiments, a metasurface array has diodes with the sensor functionality at every unit cell, or alternatively, only at a subset of unit cells distributed across the array. By having the sensor functionality at a subset of unit cells, the complexity of tuning and sensing circuitry may be kept low, while allowing a sufficient sensing of the desired parameters. In some embodiments, the sensor is implemented with a voltage sampling circuit.

In another configuration, an active metasurface antenna uses such ICs, not only with an integrated transistor for matrix drive, but also with transistor circuits that act as an RF amplifier. This creates an active metasurface that eliminates the need for a centralized low noise block downconverter (LNB) in the receive path and power amplifiers in the transmit path.

An improved design for metasurface elements of a metasurface antenna, and more specifically, tunable components of metasurface or metamaterial antennas are described herein in various embodiments. The various designs are for arrays of iris openings and unit cells on substrates, and use diodes as varactors to tune resonant frequency of the iris openings. Examples of metasurface antennas are described in U.S. Pat. No. 10,892,553, titled "Broad Tunable Bandwidth Radial Line Slot Antenna".

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Embodiments described herein will be understood more fully from the detailed description given below and from the accompanying drawings of various embodiments of the invention, which, however, should not be taken to limit the invention to the specific embodiments, but are for explanation and understanding only.

FIG. 1 illustrates one embodiment of a single junction configuration. Referring to FIG. 1, this embodiment uses a varactor diode 110 integrated with a slot antenna element (of a slotted array antenna). Diode 110 is part of integrated circuit (IC) chip 120 and has one end coupled to an RF terminal 113 that is bonded, or otherwise conductively attached, to iris metal layer 101 attached to an iris substrate (e.g., a glass substrate, etc.) (not shown) to carry RF current from one side of iris slot 102 toward the other side of iris slot 102. The other end of diode 110 is coupled in series to static capacitor 111 that is outside IC 120 in order to apply a tuning voltage. In one embodiment, static capacitor 111 is realized in one of many different forms such as, for example, a metal-insulator-metal (MIM) or interdigital capacitor (IDC).

The series circuit of diode 110 and static capacitor 111 forms a bridge across iris slot 102 of the antenna. Bias line 103 is coupled to IC chip 120 via pad 115 on IC chip 120 and applies the tuning voltage to varactor diode 110. Bias line 103 is coupled to provide a voltage from transistor 112 to pad 115 where capacitor 111 and diode 110 connect. In some embodiments, the voltage is controlled and switched by transistor 112 that is part of a matrix drive circuitry used to drive voltages to the antenna elements (e.g., RF radiating antenna elements, surface scattering metamaterial antenna elements, etc.). Alternatively, transistor 112 is part of a direct drive circuit. In some embodiments, static capacitor 111 and transistor 112 are part of the backplane that contains the drive circuitry. A thin-film transistor (TFT) can be used as transistor 112, though other types of transistors may be used (e.g., a silicon transistor, a gallium-arsenide transistor, etc.).

An RF choke 121 isolates the DC voltage on bias line 103 from the RF signal. In some other embodiments, RF choke 121 comprises an isolation resistor. In some embodiments, RF choke 121 comprises an isolation inductor. In some embodiments, RF choke 121 comprises a low pass filter.

Figure 2:
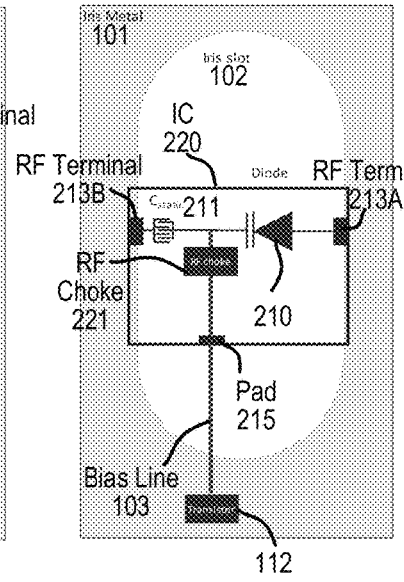
FIG. 2 illustrates some embodiments of a single junction diode IC with an integrated static capacitance.

FIG. 2 illustrates some embodiments of a single junction diode IC with an integrated static capacitance. This embodiment eliminates the static capacitor from the antenna backplane and integrates it into the diode. Due to the higher resolution and process accuracy in the diode, the static capacitance can be created with less tolerance during fabrication. The transistor that supplies the tuning voltage via a bias line is still a part of the backplane.

Referring to FIG. 2, IC chip 220 includes a varactor diode 210 coupled to static capacitor 211 in series between RF terminals 213A and 213B to form a bridge across iris slot 102 of the antenna. RF terminals 213A and 213B are bonded, or otherwise conductively attached, to iris metal layer 101 attached to an iris substrate (e.g., a glass substrate, etc.) (not shown) to carry RF current from one side of iris slot 102 to the other side of iris slot 102.

Similar to FIG. 1, bias line 103 is coupled to IC chip 220 via pad 215 on IC chip 220 and that applies the tuning voltage to varactor diode 210. Bias line 103 is coupled to provide a voltage from transistor 112 to pad 215 where capacitor 211 and diode 210 connect. In some embodiments, the tuning voltage is controlled and switched by transistor 112 that is part of a matrix drive circuitry used to drive voltages to the antenna elements (e.g., RF radiating antenna elements, surface scattering metamaterial antenna elements, etc.). Alternatively, transistor 112 is part of a direct drive circuit. A thin-film transistor (TFT) can be used as transistor 112, though other types of transistors may be used (e.g., a silicon transistor, a gallium-arsenide transistor, etc.).

An RF choke 221 isolates the DC voltage from bias line 103 from the RF signal. In some other embodiments, RF choke 221 comprises an isolation resistor. In some embodiments, RF choke 221 comprises an isolation inductor. In some embodiments, RF choke 221 comprises a low pass filter.

Figure 3:
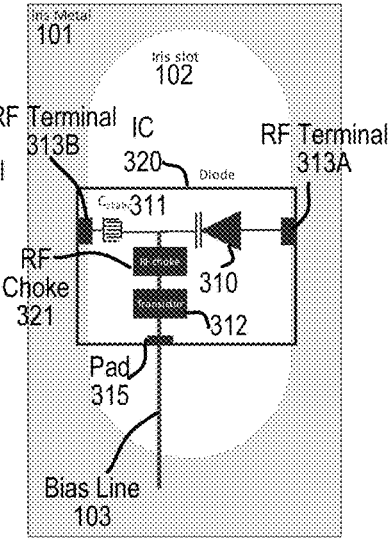
FIG. 3 illustrates one embodiment of a single junction with integrated static capacitance and integrated transistor.

FIG. 3 illustrates one embodiment of a single junction with integrated static capacitance and integrated transistor. The embodiment extends concept of FIG. 2 and eliminates the need for a backplane with transistors as the transistors are integrated on the varactor diode IC chip. In some embodiments, the circuit includes a hold-up capacitor that connects to the varactors. In one embodiment, resistive or conductive electrodes are used for connecting the transistor with the single-junction circuit.

Referring to FIG. 3, IC chip 320 includes a varactor diode 310 coupled to static capacitor 311 in series between RF terminals 313A and 313B to form a bridge across iris slot 102 of the antenna. RF terminals 313A and 313B are bonded, or otherwise conductively attached, to iris metal layer 101 attached to an iris substrate (e.g., a glass substrate, etc.) (not shown) to carry RF current from one side of iris slot 102 to the other side of iris slot 102.

IC chip 320 includes transistor 312 that is coupled to bias line 103 via pad 315 on IC chip 320. Transistor 312 receives a tuning voltage from bias line 103 and provides it to a junction where capacitor 311 and diode 310 connect. A thin-film transistor (TFT) can be used as transistor 312, though other types of transistors may be used (e.g., a silicon transistor, a gallium-arsenide transistor, etc.) and is based on the semiconductor processing of IC chip 320. In this way, transistor 312 can act as part of a matrix drive circuitry or as part of a direct drive circuit that drives voltages to the antenna elements (e.g., RF radiating antenna elements, surface scattering metamaterial antenna elements, etc.).

An RF choke 321 isolates the DC voltage from bias line 103 from the RF signal. In some other embodiments, RF choke 321 comprises an isolation resistor. In some embodiments, RF choke 321 comprises an isolation inductor. In some embodiments, RF choke 321 comprises a low pass filter.

Figure 4:
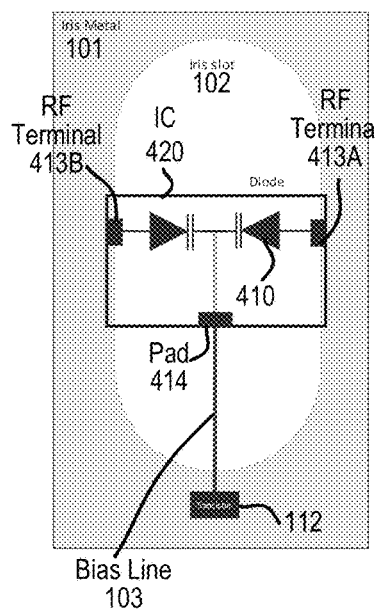
FIG. 4 illustrates some embodiments of a dual junction diode.
Figure 5:
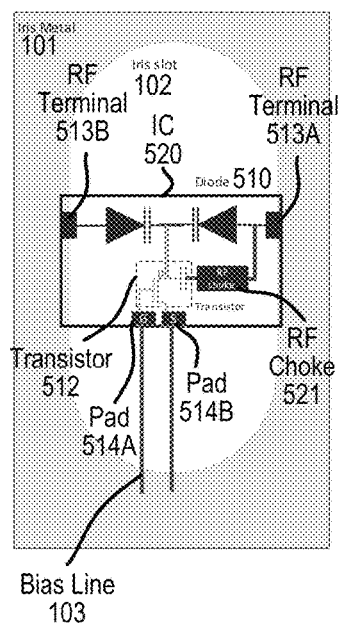
FIG. 5 illustrates one embodiment of an integrated varactor/transistor.

In some embodiments, a dual junction/common cathode approach is used instead of a single junction approach. In such a case, with the correct junction design, this configuration can completely eliminate non-linearities that can occur in the single junction approach. FIGS. 4 and 5 are examples of this type of dual junction/common cathode approach.

FIG. 4 illustrates some embodiments of a dual junction diode. Referring to FIG. 4, in some embodiments, IC chip 420 includes varactor diode device 410 that has two diodes and integrates two junction capacitors in series to bridge iris slot 102 to create a tunable capacitor for tuning the antenna. In one embodiment, the diodes share a common cathode. IC chip 420 also includes two RF terminals 413A and 413B coupled to the series connection of the two diodes with integrated capacitors to form a bridge for RF current across iris slot 102 of the antenna. RF terminals 413A and 413B are bonded, or otherwise conductively attached, to iris metal layer 101 attached to an iris substrate (e.g., a glass substrate, etc.) (not shown) to carry RF current from one side of iris slot 102 to the other side of iris slot 102. A third terminal, pad 414, is included that inserts a tuning voltage at the connection point between the two junctions. In some embodiments, the voltage is controlled and switched by transistor 112 that is part of backplane and the drive circuit (e.g., matrix drive circuit, direct drive circuit, etc.).

In some embodiments, a hold-up capacitor (not shown in FIG. 4) is used in addition to transistor 112 as part of the backplane of the antenna. This may be coupled to an iris metal layer of an iris substrate. In one embodiment, transistor 112 is a TFT. An iris with a dual-junction capacitor requires a diode with a much lower capacitance tuning ratio. While the single junction requires a capacitance ratio of about 1:8 to cover the tuning bandwidth of a Ku-band or Ka-band antenna, the dual junction embodiment uses a capacitance ratio in the range of 1:2 to 1:3. The reduction in the tuning ratio allows the Q-factor of the diode to increase drastically, thereby improving the antenna radiation efficiency.

FIG. 5 illustrates one embodiment of an integrated varactor/transistor. This embodiment extends the dual junction circuit described above in FIG. 4 and integrates the transistor that acts as the switch for the diode into the chip. There are different ways to design the transistor circuit. An example is shown in FIG. 5. This concept eliminates the need for a backplane with transistors to drive the tuning voltages as they are integrated in the varactor diode chip. In one embodiment, the circuit includes a hold-up capacitor that connects to the varactors. In some embodiments, resistive or conductive electrodes are used for connecting the transistor with the dual junction circuit.

Referring to FIG. 5, in one embodiment, IC chip 520 includes varactor diode device 510 that has two diodes and integrates two junction capacitors in series to bridge iris slot 102 to create a tunable capacitor for tuning the antenna. In one embodiment, the diodes share a common cathode. IC chip 520 also includes two RF terminals 513A and 513B coupled to the series connection of the two diodes with integrated capacitors to form a bridge for RF current across iris slot 102 of the antenna. RF terminals 513A and 513B are bonded, or otherwise conductively attached, to iris metal layer 101 attached to an iris substrate (e.g., a glass substrate, etc.) (not shown) to carry RF current from one side of iris slot 102 to the other side of iris slot 102. A third terminal, pad 514A, is included that applies a tuning voltage to a gate of transistor 512 that is also part of IC chip 520. In some embodiments, the tuning voltage is applied to the gate of transistor 512 via bias line 103 that is part of backplane and the drive circuit (e.g., matrix drive circuit, direct drive circuit, etc.). Another terminal, pad 514B couples the source of transistor 512 to the column controller 1502 in FIG. 15. The drain of transistor 512 is connected in series with a capacitor and a RF choke 521. The end of RF choke 521 is connected to RF terminal 513A.

An RF choke 521 isolates the DC voltage from bias line 103 from the RF signal. In some other embodiments, RF choke 521 comprises an isolation resistor. In some embodiments, RF choke 521 comprises an isolation inductor. In some embodiments, RF choke 521 comprises a low pass filter.

Figure 6:
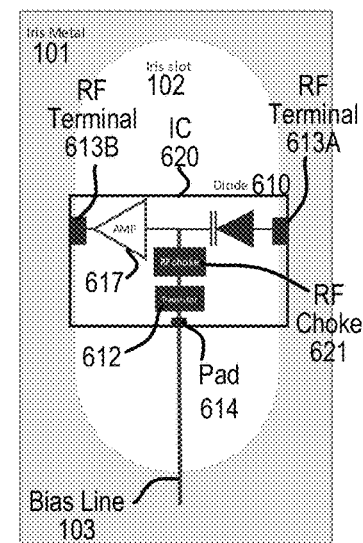
FIG. 6 illustrates one embodiment of an integrated varactor/transistor/amplifier.

FIG. 6 illustrates one embodiment of an integrated varactor/transistor/amplifier. This embodiment integrates an RF amplifier into a diode chip, in conjunction with the varactor diode and the transistor circuit. The amplifier is responsible for amplifying the signal received or transmitted through the slot antenna element. Once a wave couples to the slot antenna element, currents and voltages are induced in the slot antenna element, which are amplified before passing through. The varactor diode has the same functionality as discussed above, which is the tuning of the resonance frequency of the slot antenna element. Using such an embodiment, an active metasurface antenna does not need to have an amplifier in the RF chain. Furthermore, the integration of the amplifier allows for controlling the amplitude of the transmitted power independently from the phase adjusted by the varactor. This results in a higher performance of the antenna or will allow for the reduction in the density of the array.

Referring to FIG. 6, IC chip 620 includes a varactor diode 610 coupled to amplifier 617 in series between RF terminals 613A and 613B to form a bridge across iris slot 102 of the antenna. RF terminals 613A and 613B are bonded, or otherwise conductively attached, to iris metal layer 101 attached to an iris substrate (e.g., a glass substrate, etc.) (not shown) to carry RF current from one side of iris slot 102 to the other side of iris slot 102.

IC chip 620 includes transistor 612 that is coupled to bias line 103 via pad 614 on IC chip 620. Transistor 612 receives a tuning voltage from bias line 103 and provides it to a junction where amplifier 617 and diode 610 connect. A thin-film transistor (TFT) can be used as transistor 612, though other types of transistors may be used (e.g., a silicon transistor, a gallium-arsenide transistor, etc.) and is based on the semiconductor processing of IC chip 620. In this way, transistor 612 can act as part of a matrix drive circuitry or as part of direct drive circuitry that drives voltages to the antenna elements (e.g., RF radiating antenna elements, surface scattering metamaterial antenna elements, etc.).

An RF choke 621 is coupled between transistor 612 and the connection between diode 610 and amplifier 617. RF choke 621 isolates the DC voltage from bias line 103 from the RF signal. In some other embodiments, RF choke 521 comprises an isolation resistor. In some embodiments, RF choke 521 comprises an isolation inductor. In some embodiments, RF choke 521 comprises a low pass filter.

In combined receive/transmit apertures (e.g., apertures having both transmit and receive antenna elements (e.g., RF radiating antenna elements, surface scattering metamaterial antenna elements, etc.)), the amplifiers can be integrated in the metasurface either for both receive and transmit or just for one of them depending on the use case.

Different amplifier classes and architectures can be conceived and implemented for this category, including negative impedance converters.

Figure 7:
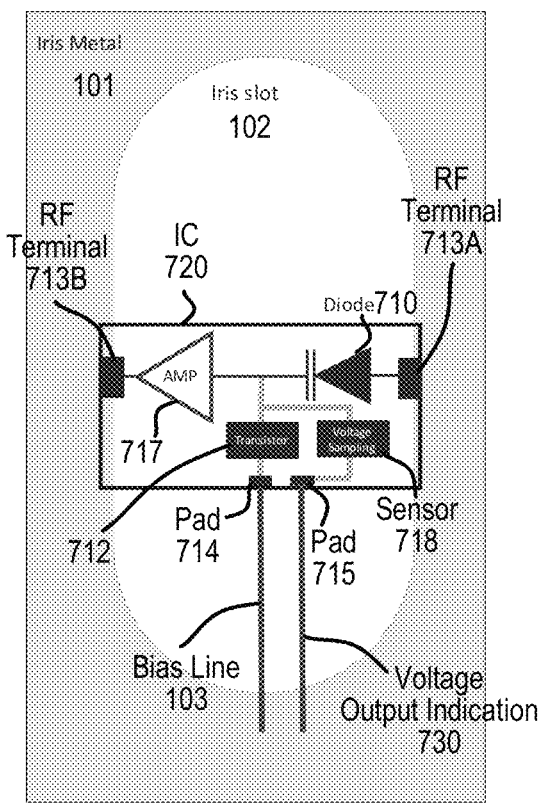
FIG. 7 illustrates one embodiment of an integrated varactor/transistor/sensor (e.g., voltage sampling).

FIG. 7 illustrates one embodiment of an integrated varactor/transistor/sensor (e.g., voltage sampling). This embodiment integrates a sensor (e.g., a voltage sampling circuit, etc.) into the diode chip along with the transistor to read the voltage on the diode. This will allow in-field calibration of the drive voltages based on environmental changes or variations in device characteristics. The integration of the sensor/voltage sampling circuit is shown in FIG. 7 for a diode chip which integrates a varactor, a transistor, and an amplifier. However, it can also be integrated to all the other configurations shown in FIGS. 1-6 that are described above.

Referring to FIG. 7, IC chip 720 includes a varactor diode 710 coupled to amplifier 717 in series between RF terminals 713A and 713B to form a bridge across iris slot 102 of the antenna. RF terminals 713A and 713B are bonded, or otherwise conductively attached, to iris metal layer 101 attached to an iris substrate (e.g., a glass substrate, etc.) (not shown) to carry RF current from one side of iris slot 102 to the other side of iris slot 102.

IC chip 720 includes transistor 712 that is coupled to bias line 103 via pad 714 on IC chip 720. Transistor 712 receives a tuning voltage from bias line 103 and provides it to a junction where amplifier 717 and diode 710 connect. A thin-film transistor (TFT) can be used as transistor 712, though other types of transistors may be used (e.g., a silicon transistor, a gallium-arsenide transistor, etc.) and is based on the semiconductor processing of IC chip 720. In this way, transistor 712 can act as part of a matrix drive circuitry or as part of direct drive circuitry that drives voltages to the antenna elements (e.g., RF radiating antenna elements, surface scattering metamaterial antenna elements, etc.).

Sensor 718, in the form of a voltage sampling circuit, is coupled pad 715 and the output of transistor 712 and samples the voltage output from transistor 712. In some embodiments, the sensed voltage is sent, via pad 715, to an antenna control unit (ACU) for use in calibrating the tuning voltages. For example, if the tuning voltage to be applied to diode 710 via bias line 103 is to be 10V and the output of transistor 712 is 9.8V, the voltage from the drive circuitry can be adjusted to ensure that the voltage output from transistor 712 is 10V.

Figure 8:
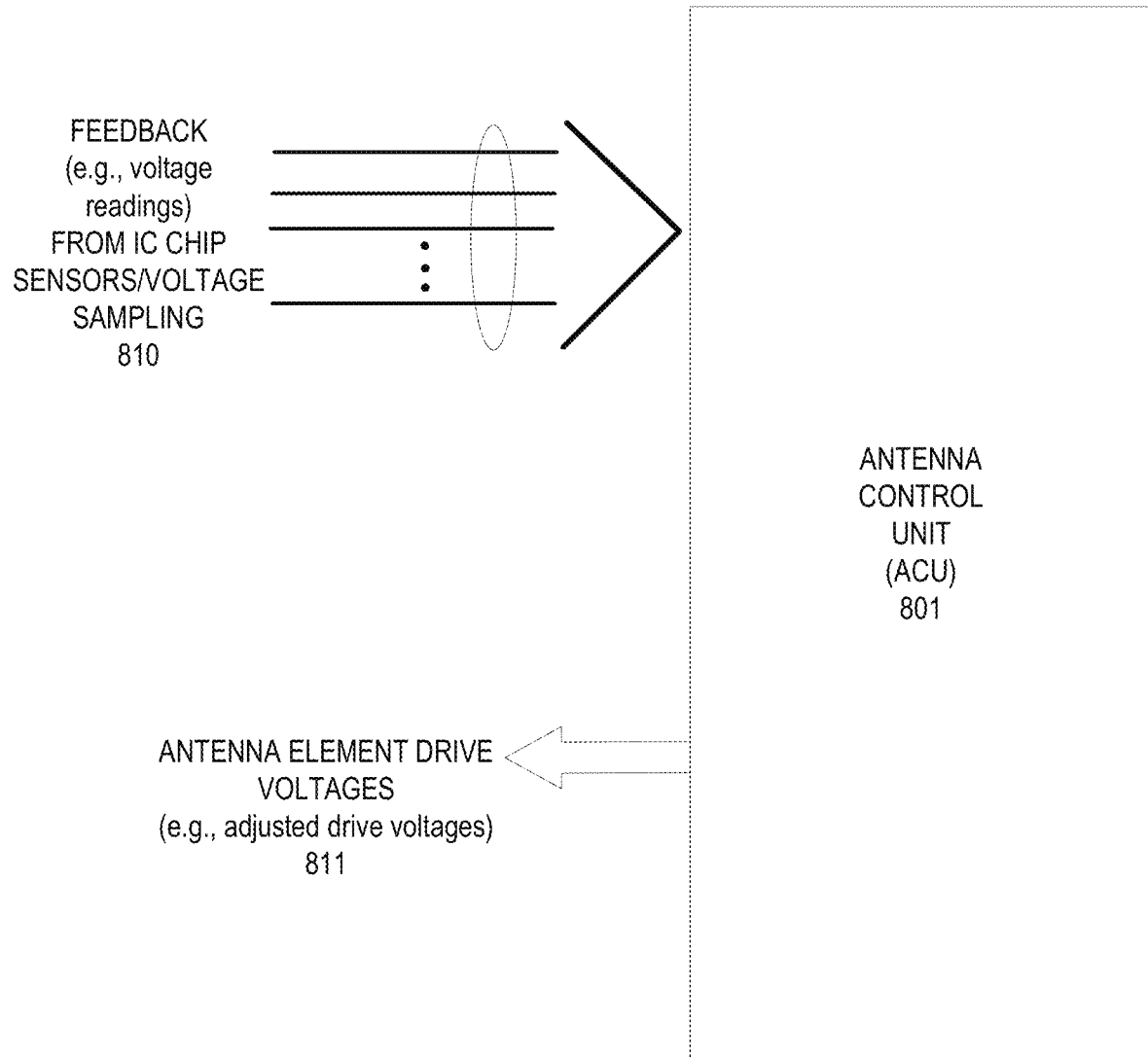
FIG. 8 illustrates some embodiments of an antenna control unit (ACU).

FIG. 8 illustrates some embodiments of an antenna control unit (ACU). Referring to FIG. 8, ACU 801 receives feedback 810 that comprise tuning voltage readings taken by sensors on IC chips, such as, for example, the IC chips containing varactor diodes for tuning antenna elements. In response to feedback 810, ACU 801 generates antenna element drive voltages or indications of those voltages 811 for use in tuning the antenna elements. In the case of voltage indications, ACU 801 can provide these to drive circuitry (e.g., matrix drive circuitry, direct drive circuitry, etc.) that using the indications to create and drive tuning voltages to the antenna elements. The generation of these voltages can be done, based and/or in cooperation with control patterns generated to control the antenna elements.

Figure 9:
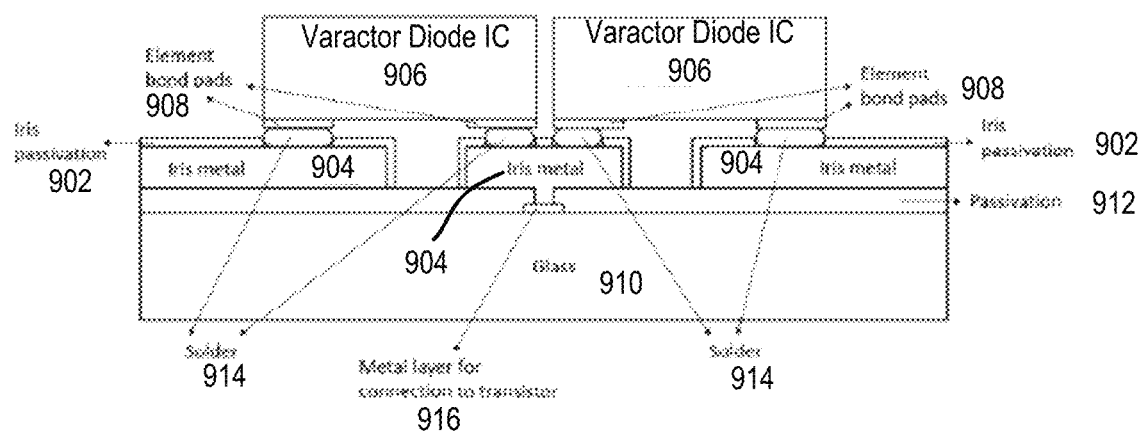
FIG. 9 is a cross section view of the diode-TFT array-iris connection.

FIG. 9 is a cross section view of the diode-TFT array-iris connection. In one embodiment, the fabrication starts with creating the TFT matrix on a glass substrate 910. Illustratively, any one of a variety of TFT fabrication techniques may be utilized. Layers used for TFT matrix fabrication typically include multiple metal layers for electrical connection and multiple dielectric layers for passivation. For this method, TFT array fabrication ends with a passivation layer 912 covering the TFT matrix. Openings that align to the iris interconnect area are created in this passivation layer 912 where varactor diode IC 906 are later connected to the TFT matrix. Additionally, a metal trace 916 aligning to the opening in the passivation layer 912 and the iris interconnect is patterned to make the connection to the TFT matrix. One of the metal layers in TFT matrix fabrication (e.g., gate metal, source metal) can be used for this connection.

In one embodiment, an iris metal 904 layer is a few micrometers thick and it is deposited on a glass substrate 910 using sputtering, electroplating or e-beam evaporation for example, or other process that may be devised. This metal layer is later etched to create iris slots, or openings, where all the metal in the iris opening area is removed. Illustratively, the iris metal is deposited on a glass substrate 910 which already has a TFT matrix patterned on it. Additionally, a portion of the iris metal layer, generally referred to as the iris interconnect, is kept for electrical connection between the varactor diode IC 906 and the TFT matrix. The iris metal 904 and the iris interconnect are protected by an iris passivation layer 902, which is a dielectric layer (e.g., SiNx).

Still further, openings are created in the iris passivation layer for connecting the varactor diode IC 906 through respective element bond pads 908 to the iris metal 904 and the iris interconnect. This connection to the bonding or bond pads 908 of the varactor diode IC 906 can be made using a solder 914. Alternatively, such connections between bonding pads of the tunable elements and iris metal in this and other disclosed embodiments may be made with conductive paste, conductive polymer, conductive epoxy, silver epoxy, etc. in place of solder. Discrete parts can be assembled to this substrate using various methods, such as, but not limited to, pick-and-place, self-assembly, etc.

Varactor diode IC 906 can be in a rectangular shape. One skilled in the art will appreciate, however, the aspects of the present application are not limited to rectangular discrete elements. They might have different shapes such as, for example, a circle, triangle, etc. Bonding pads on the varactor diode IC 906 can also reside on different faces. For example, a bonding pad may reside on the top surface and another bonding pad may reside on the bottom surface. Bonding pads may cover part of the surface or the whole surface. In this case, first electrical connection is made with a conductive paste or solder like the method described above and the second electrical connection is achieved by deposition of an additional metal layer to connect the top electrode to the iris.

Figure 10:
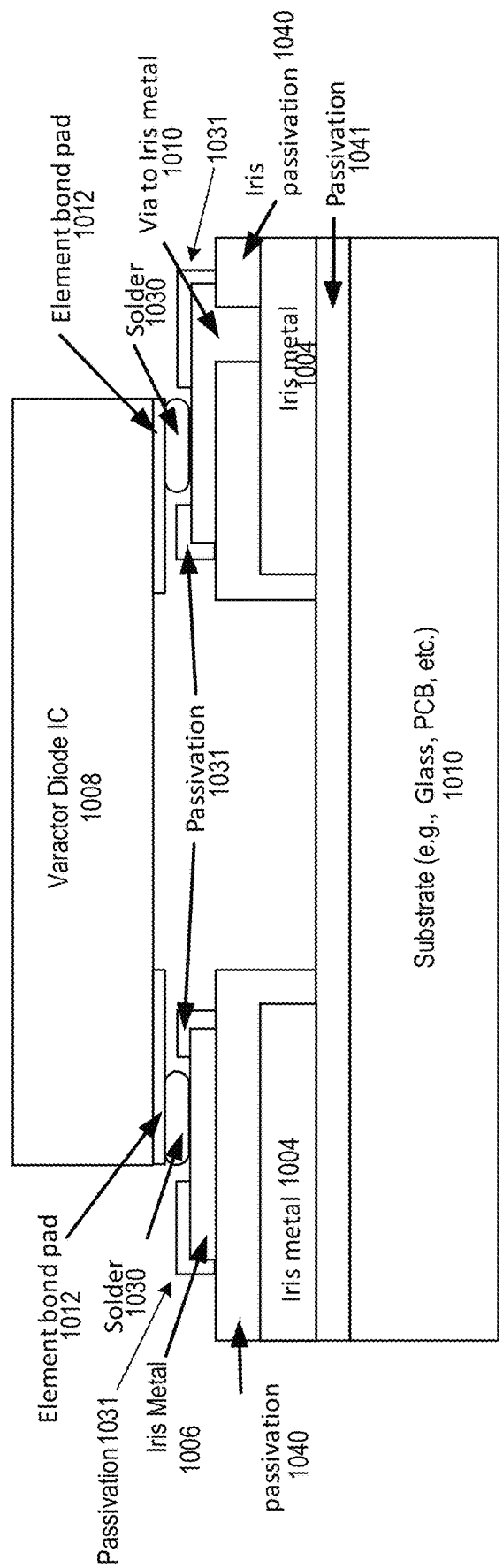
FIG. 10 is a cross section view of the diode-TFT array-iris connection.

FIG. 10 is a cross section view of the diode-TFT array-iris connection. In some embodiments, the fabrication starts with creating the TFT matrix on a glass substrate 1010. Illustratively, any one of a variety of TFT fabrication techniques may be utilized. Layers used for TFT matrix fabrication typically include multiple metal layers for electrical connection and multiple dielectric layers for passivation. For this method, TFT array fabrication ends with a passivation layer 1041 covering the TFT matrix. Openings are created in that passivation layer 1040 which align to a via structure connecting a TFT array to the iris metal 1006. Iris metal 1006 are formed on a metal layer separate from iris metal layer. An opening in the iris metal layer, separate from the iris opening, is created in the TFT array-to-iris metal 1006 via location. This via structure isn't shown in FIG. 10. Metal traces connecting each TFT to a driver IC, i.e. row traces and column traces in a TFT matrix, can be fabricated either below the iris metal using the metal layers for the TFT matrix or above the iris metal using additional metal layers.

In some embodiments, an iris metal layer 1004 (i.e., a metal layer in which the iris opening is formed) is a few micrometers thick and it is deposited on a glass substrate 1010 using sputtering, electroplating or e-beam evaporation. This metal layer is later etched to create iris slot, or opening, 1004 where all the metal in the iris opening area is removed. Illustratively, the iris metal is deposited on a glass substrate 1010 that already has a TFT matrix patterned on it. The iris metal layer in which iris openings 1004 are formed is protected by an iris passivation layer 1031, which is in some embodiments, for example, a dielectric layer (e.g., SiNx). In a further embodiment, the TFT matrix (e.g., circuitry with thin film transistors) is deposited above the iris metal, for example on top of the iris passivation layer 1031.

Still further, openings are created in the iris passivation layer for connecting the pad 1012 on iris metal layer 1006 to other iris metal. Additional openings including via 1010 are created in the passivation layer 1031 covering the iris metal layer 1006 to connect the iris metal layer 1010 and the pad 1012 to varactor diode IC 1008 through respective element bond pads 1012. This connection to the bonding or bond pads 1012 of varactor diode IC 1008 can be made using a solder 1030. Alternative, such connections between bonding pads of the tunable elements and iris metal in this and other disclosed embodiments may be made with conductive paste, polymer, conductive epoxy, silver epoxy, etc. in place of solder. Discrete parts can be assembled to this substrate using various methods, such as, but not limited to, pick-and-place, self-assembly, etc.

Varactor diode IC 1008 is shown in a rectangular shape in FIG. 10. One skilled in the art will appreciate, however, the aspects of the present application are not limited to rectangular discrete elements. They might have different shapes such as, for example, a circle, triangle, etc. Bonding pads on varactor diode IC 1008 can also reside on different faces. For example, a bonding pad may reside on the top surface and another bonding pad may reside on the bottom surface. Bonding pads may cover part of the surface or the whole surface. In this case, first electrical connection is made with a conductive paste or solder like the method described above and the second electrical connection is achieved by deposition of an additional metal layer to connect the top electrode to the iris.

FIG. 11 is a flow diagram of some embodiments of a process for using a varactor diode device for controlling an antenna element of an antenna. The antenna elements may be RF radiating antenna elements, surface scattering metamaterial antenna elements, etc., while the antenna can be a satellite communications antenna for a satellite terminal or other wireless device antenna.

Referring to FIG. 11, the process begins by receiving a tuning voltage on an IC chip having a varactor diode device from a transistor (1101). The varactor diode device can be, such as disclosed herein, a single varactor diode, a single varactor diode with a capacitor as a DC block, a pair of varactor diodes, or another tuning device in an IC chip. The transistor can be a transistor off the IC chip or transistor on the IC chip, such as disclosed herein.

The process also includes adjusting RF characteristics of an antenna element coupled to the IC chip by applying the tuning voltage to the varactor diode (1102). For example, the RF characteristics of the antenna element may be changed based on the tuning voltage applied to the varactor diode to tune the antenna element.

After receiving and while applying the tuning voltage to the varactor diode, the process senses the tuning voltage to be applied to the varactor diode device using a sensor (e.g., voltage sampling circuitry) on the IC chip and thereafter sends sensing results (e.g., sensed voltage, indications of a sensed voltage) back to a control unit off the IC chip (1103). In some embodiments, the sensor includes voltage sampling circuitry on the IC chip. In some embodiments, the sensor sends a sensed voltage back to the antenna control unit (ACU). In some other embodiments, the sensor sends an indication of the sensed voltage back to the ACU. The ACU may use the results of sensing to adjust the tuning voltage that is applied to the antenna element or to other antenna elements in the antenna. The latter case occurs when only some of the antenna elements have sensors to measure the voltage being applied to the varactor diode for tuning.

In some embodiments, the process includes amplifying an RF signal received or transmitted through an iris slot of the antenna element using an amplifier on the IC chip (1104). In order words, if the iris slot of antenna element is used for receiving an RF signal, the RF signal is amplified by the amplifier on the IC chip while receiving the RF signal, and if the iris slot of antenna element is used for transmitting an RF signal, the RF signal is amplified by the amplifier on the IC chip while transmitting the RF signal.

Examples of Antenna Embodiments

The techniques described above may be used with flat panel satellite antennas. Embodiments of such flat panel antennas are disclosed. The flat panel antennas include one or more arrays of antenna elements on an antenna aperture. In one embodiment, the antenna aperture is a metasurface antenna aperture, such as, for example, the antenna apertures described below. In one embodiment, the antenna elements comprise diodes and varactors such as described above. In one embodiment, the flat panel antenna is a cylindrically fed antenna that includes matrix drive circuitry to uniquely address and drive each of the antenna elements that are not placed in rows and columns. In one embodiment, the elements are placed in rings.

In one embodiment, the antenna aperture having the one or more arrays of antenna elements is comprised of multiple segments coupled together. When coupled together, the combination of the segments form closed concentric rings of antenna elements. In one embodiment, the concentric rings are concentric with respect to the antenna feed.

Figure 12:
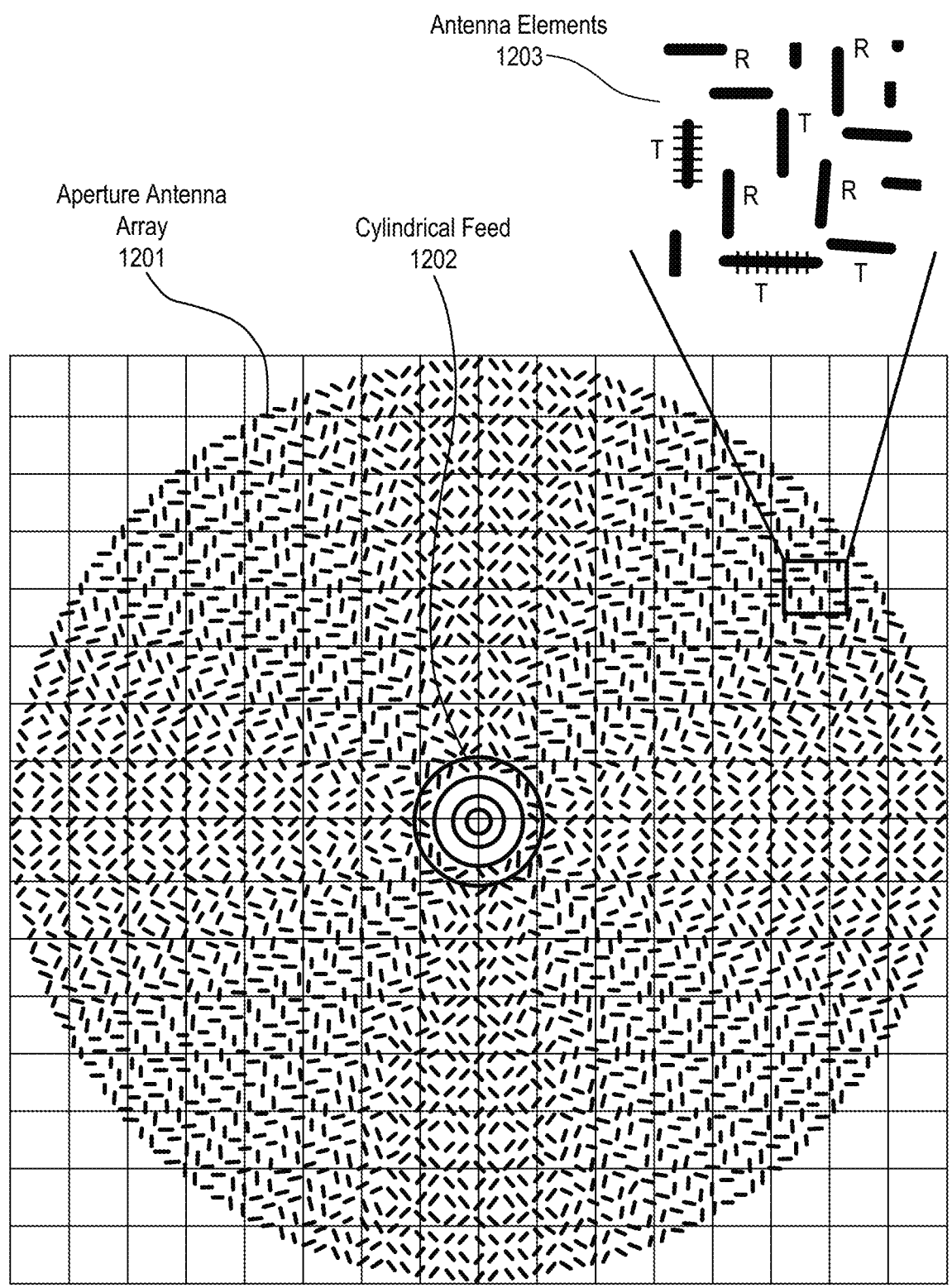
FIG. 12 illustrates the schematic of one embodiment of a cylindrically fed holographic radial aperture antenna.

FIG. 12 illustrates the schematic of one embodiment of a cylindrically fed holographic radial aperture antenna. Referring to FIG. 12, the antenna aperture has one or more arrays 1201 of antenna elements 1203 that are placed in concentric rings around an input feed 1202 of the cylindrically fed antenna. In one embodiment, antenna elements 1203 are radio frequency (RF) resonators that radiate RF energy. In one embodiment, antenna elements 1203 comprise both Rx and Tx irises that are interleaved and distributed on the whole surface of the antenna aperture. Such Rx and Tx irises, or slots, may be in groups of three or more sets where each set is for a separately and simultaneously controlled band. Examples of such antenna elements with irises are described in greater detail below. Note that the RF resonators described herein may be used in antennas that do not include a cylindrical feed.

In one embodiment, the antenna includes a coaxial feed that is used to provide a cylindrical wave feed via input feed 1202. In one embodiment, the cylindrical wave feed architecture feeds the antenna from a central point with an excitation that spreads outward in a cylindrical manner from the feed point. That is, a cylindrically fed antenna creates an outward travelling concentric feed wave. Even so, the shape of the cylindrical feed antenna around the cylindrical feed can be circular, square or any shape. In another embodiment, a cylindrically fed antenna creates an inward travelling feed wave. In such a case, the feed wave most naturally comes from a circular structure.

In one embodiment, antenna elements 1203 comprise irises (iris openings) and the aperture antenna of FIG. 12 is used to generate a main beam shaped by using excitation from a cylindrical feed wave for radiating the iris openings through tunable diodes and/or varactors. In one embodiment, the antenna can be excited to radiate a horizontally or vertically polarized electric field at desired scan angles.

In one embodiment, each scattering element in the antenna system is part of a unit cell as described above. In one embodiment, the unit cell is driven by the direct drive embodiments described above. In one embodiment, the diode/varactor in each unit cell has a lower conductor associated with an iris slot from an upper conductor associated with its tuning electrode (e.g., iris metal). The diode/varactor can be controlled to adjust the bias voltage between the iris opening and the patch electrode. Using this property, in one embodiment, the diode/varactor integrates an on/off switch for the transmission of energy from the guided wave to the unit cell. When switched on, the unit emits an electromagnetic wave like an electrically small dipole antenna. Note that the teachings herein are not limited to having unit cell that operates in a binary fashion with respect to energy transmission.

In one embodiment, the feed geometry of this antenna system allows the antenna elements to be positioned at forty-five-degree (45°) angles to the vector of the wave in the wave feed. Note that other positions may be used (e.g., at 40° angles). This position of the elements enables control of the free space wave received by or transmitted/radiated from the elements. In one embodiment, the antenna elements are arranged with an inter-element spacing that is less than a free-space wavelength of the operating frequency of the antenna. For example, if there are four scattering elements per wavelength, the elements in the 30 GHz transmit antenna will be approximately 2.5 mm (i.e., ¼th the 10 mm free-space wavelength of 30 GHz).

In one embodiment, the two sets of elements are perpendicular to each other and simultaneously have equal amplitude excitation if controlled to the same tuning state. Rotating them +/−45 degrees relative to the feed wave excitation achieves both desired features at once. Rotating one set 0 degrees and the other 90 degrees would achieve the perpendicular goal, but not the equal amplitude excitation goal. Note that 0 and 90 degrees may be used to achieve isolation when feeding the array of antenna elements in a single structure from two sides.

The amount of radiated power from each unit cell is controlled by applying a voltage to the patch electrode using a controller. Traces to each patch electrode are used to provide the voltage to the patch electrode. The voltage is used to tune or detune the capacitance and thus the resonance frequency of individual elements to effectuate beam forming. The voltage required is dependent on the diode/varactor being used.

In one embodiment, as discussed above, a matrix drive is used to apply voltage to the patch electrodes in order to drive each cell separately from all the other cells without having a separate connection for each cell (direct drive). Because of the high density of elements, the matrix drive is an efficient way to address each cell individually.

In one embodiment, the control structure for the antenna system has two main components: the antenna array controller, which includes drive electronics for the antenna system, is below the wave scattering structure of surface scattering antenna elements such as described herein, while the matrix drive switching array is interspersed throughout the radiating RF array in such a way as to not interfere with the radiation. In one embodiment, the drive electronics for the antenna system comprise commercial off-the shelf LCD controls used in commercial television appliances that adjust the bias voltage for each scattering element by adjusting the amplitude or duty cycle of an AC bias signal to that element.

In one embodiment, the antenna array controller also contains a microprocessor executing the software. The control structure may also incorporate sensors (e.g., a GPS receiver, a three-axis compass, a 3-axis accelerometer, 3-axis gyro, 3-axis magnetometer, etc.) to provide location and orientation information to the processor. The location and orientation information may be provided to the processor by other systems in the earth station and/or may not be part of the antenna system.

More specifically, the antenna array controller controls which elements are turned off and those elements turned on and at which phase and amplitude level at the frequency of operation. The elements are selectively detuned for frequency operation by voltage application.

For transmission, a controller supplies an array of voltage signals to the RF patches to create a modulation, or control pattern. The control pattern causes the elements to be turned to different states. In one embodiment, multistate control is used in which various elements are turned on and off to varying levels, further approximating a sinusoidal control pattern, as opposed to a square wave (i.e., a sinusoid gray shade modulation pattern). In one embodiment, some elements radiate more strongly than others, rather than some elements radiate and some do not. Variable radiation is achieved by applying specific voltage levels, which adjusts the liquid crystal permittivity to varying amounts, thereby detuning elements variably and causing some elements to radiate more than others.

The generation of a focused beam by the metamaterial array of elements can be explained by the phenomenon of constructive and destructive interference. Individual electromagnetic waves sum up (constructive interference) if they have the same phase when they meet in free space, and waves cancel each other (destructive interference) if they are in opposite phase when they meet in free space. If the slots in a slotted antenna are positioned so that each successive slot is positioned at a different distance from the excitation point of the guided wave, the scattered wave from that element will have a different phase than the scattered wave of the previous slot. If the slots are spaced one quarter of a guided wavelength apart, each slot will scatter a wave with a one fourth phase delay from the previous slot.

Using the array, the number of patterns of constructive and destructive interference that can be produced can be increased so that beams can be pointed theoretically in any direction plus or minus ninety degrees (90°) from the bore sight of the antenna array, using the principles of holography. Thus, by controlling which metamaterial unit cells are turned on or off (i.e., by changing the pattern of which cells are turned on and which cells are turned off), a different pattern of constructive and destructive interference can be produced, and the antenna can change the direction of the main beam. The time required to turn the unit cells on and off dictates the speed at which the beam can be switched from one location to another location.

In one embodiment, the antenna system produces one steerable beam for the uplink antenna and one steerable beam for the downlink antenna. In one embodiment, the antenna system uses metamaterial technology to receive beams and to decode signals from the satellite and to form transmit beams that are directed toward the satellite. In one embodiment, the antenna systems are analog systems, in contrast to antenna systems that employ digital signal processing to electrically form and steer beams (such as phased array antennas). In one embodiment, the antenna system is considered a "surface" antenna that is planar and relatively low profile, especially when compared to conventional satellite dish receivers.

Figure 13A:
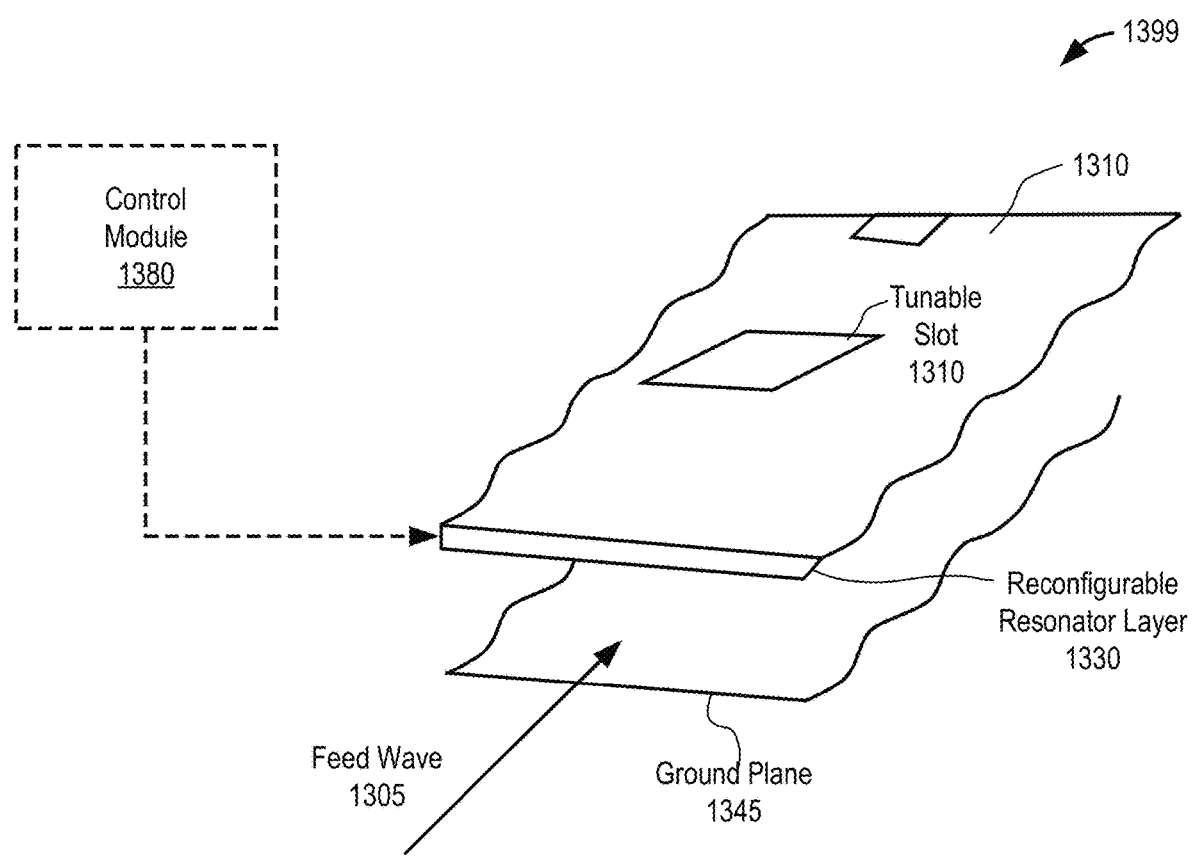
FIG. 13A illustrates a perspective view of one row of antenna elements that includes a ground plane and a reconfigurable resonator layer.

FIG. 13A illustrates a perspective view of one row of antenna elements that includes a ground plane 1345 and a reconfigurable resonator layer 1330. Reconfigurable resonator layer 1330 includes an array 1312 of tunable slots 1310. The array 1312 of tunable slots 1310 can be configured to point the antenna in a desired direction. Each of the tunable slots 1310 can be tuned/adjusted by varying a voltage, which changes the capacitance of the varactor diode and results in a frequency shift, which in turn changes the amplitude and phase of the radiating antenna element. A proper phase and amplitude adjustment of the antenna elements in an array will result in a beam formation and beam steering.

Control module 1380, or a controller, is coupled to reconfigurable resonator layer 1330 to modulate the array 1312 of tunable slots 1310 by varying the voltage to the diodes/varactors. Control module 1380 may include a Field Programmable Gate Array ("FPGA"), a microprocessor, a controller, System-on-a-Chip (SoC), or other processing logic. In one embodiment, control module 1380 includes logic circuitry (e.g., multiplexer) to drive the array 1312 of tunable slots 1310. In one embodiment, control module 1380 receives data that includes specifications for a holographic diffraction pattern to be driven onto the array 1312 of tunable slots 1310. The holographic diffraction patterns may be generated in response to a spatial relationship between the antenna and a satellite so that the holographic diffraction pattern steers the downlink beams (and uplink beam if the antenna system performs transmit) in the appropriate direction for communication. Although not drawn in each figure, a control module similar to control module 1380 may drive each array of tunable slots described in various embodiments in the disclosure.

Radio Frequency ("RF") holography is also possible using analogous techniques where a desired RF beam can be generated when an RF reference beam encounters an RF holographic diffraction pattern. In the case of satellite communications, the reference beam is in the form of a feed wave, such as feed wave 1305 (approximately 20 GHz in some embodiments). To transform a feed wave into a radiated beam (either for transmitting or receiving purposes), an interference pattern is calculated between the desired RF beam (the object beam) and the feed wave (the reference beam). The interference pattern is driven onto the array of tunable slots 1310 as a diffraction pattern so that the feed wave is "steered" into the desired RF beam (having the desired shape and direction). In other words, the feed wave encountering the holographic diffraction pattern "reconstructs" the object beam, which is formed according to design requirements of the communication system. The holographic diffraction pattern contains the excitation of each element and is calculated by $w_{hologram} = w^*_{in} w_{out}$, with $w_{in}$ as the wave equation in the waveguide and $w_{out}$ the wave equation on the outgoing wave.

A voltage between the patch electrode and the iris opening can be modulated to tune the antenna element (e.g., the tunable resonator/slot). Adjusting the voltage varies the capacitance of a slot (e.g., the tunable resonator/slot). Accordingly, the reactance of a slot (e.g., the tunable resonator/slot) can be varied by changing the capacitance. Resonant frequency of the slot also changes according to the equation $$f = \frac{1}{2\pi\sqrt{LC}}$$

where f is the resonant frequency of the slot and L and C are the inductance and capacitance of the slot, respectively. The resonant frequency of the slot affects the energy radiated from feed wave 1305 propagating through the waveguide. As an example, if feed wave 1305 is 20 GHz, the resonant frequency of a slot 1310 may be adjusted (by varying the capacitance) to 17 GHz so that the slot 1310 couples substantially no energy from feed wave 1305. Or, the resonant frequency of a slot 1310 may be adjusted to 20 GHz so that the slot 1310 couples energy from feed wave 1305 and radiates that energy into free space. Although the examples given are binary (fully radiating or not radiating at all), full gray scale control of the reactance, and therefore the resonant frequency of slot 1310 is possible with voltage variance over a multi-valued range. Hence, the energy radiated from each slot 1310 can be finely controlled so that detailed holographic diffraction patterns can be formed by the array of tunable slots.

In one embodiment, tunable slots in a row are spaced from each other by λ/5. Other spacings may be used. In one embodiment, each tunable slot in a row is spaced from the closest tunable slot in an adjacent row by λ/2, and, thus, commonly oriented tunable slots in different rows are spaced by λ/4, though other spacings are possible (e.g., λ/5, λ/6.3). In another embodiment, each tunable slot in a row is spaced from the closest tunable slot in an adjacent row by λ/3.

Figure 13B:
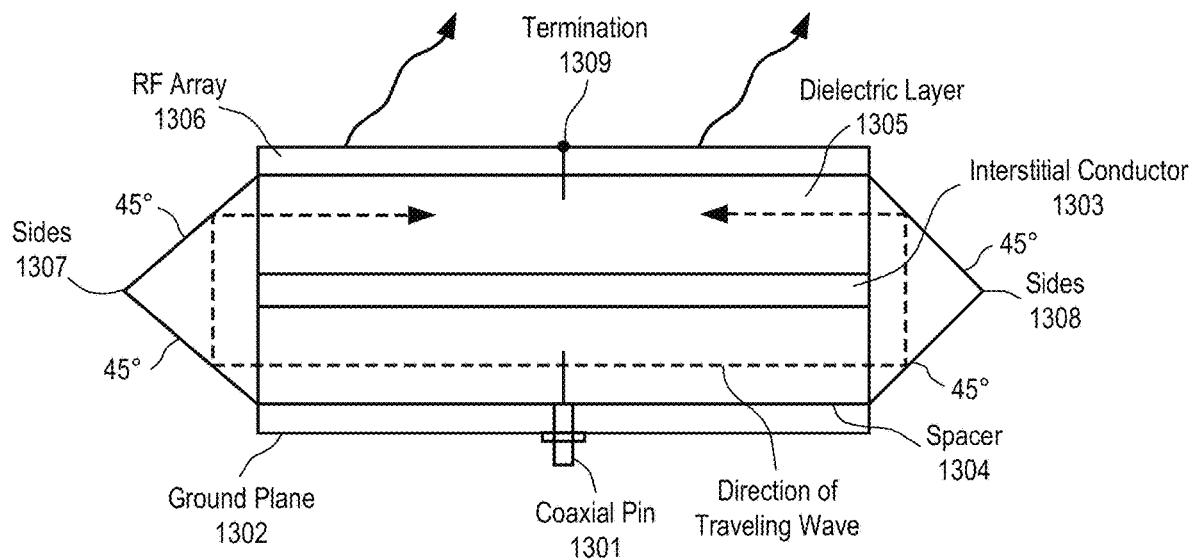
FIG. 13B illustrates a side view of one embodiment of a cylindrically fed antenna structure.

FIG. 13B illustrates a side view of one embodiment of a cylindrically fed antenna structure. The antenna produces an inwardly travelling wave using a double layer feed structure (i.e., two layers of a feed structure). In one embodiment, the antenna includes a circular outer shape, though this is not required. That is, non-circular inward travelling structures can be used. In one embodiment, the antenna structure in FIG. 13B includes a coaxial feed, such as, for example, described in U.S. Publication No. 2015/0236412, entitled "Dynamic Polarization and Coupling Control from a Steerable Cylindrically Fed Holographic Antenna", filed on Nov. 21, 2014.

Referring to FIG. 13B, a coaxial pin 1301 is used to excite the field on the lower level of the antenna. In one embodiment, coaxial pin 1301 is a 50Ω coax pin that is readily available. Coaxial pin 1301 is coupled (e.g., bolted) to the bottom of the antenna structure, which is conducting ground plane 1302.

Separate from conducting ground plane 1302 is interstitial conductor 1303, which is an internal conductor. In one embodiment, conducting ground plane 1302 and interstitial conductor 1303 are parallel to each other. In one embodiment, the distance between ground plane 1302 and interstitial conductor 1303 is 0.1-0.15". In another embodiment, this distance may be λ/2, where λ is the wavelength of the travelling wave at the frequency of operation.

Ground plane 1302 is separated from interstitial conductor 1303 via a spacer 1304. In one embodiment, spacer 1304 is a foam or air-like spacer. In one embodiment, spacer 1304 comprises a plastic spacer.

On top of interstitial conductor 1303 is dielectric layer 1305. In one embodiment, dielectric layer 1305 is plastic.

The purpose of dielectric layer 1305 is to slow the travelling wave relative to free space velocity. In one embodiment, dielectric layer 1305 slows the travelling wave by 30% relative to free space. In one embodiment, the range of indices of refraction that are suitable for beam forming are 1.2-1.8, where free space has by definition an index of refraction equal to 1. Other dielectric spacer materials, such as, for example, plastic, may be used to achieve this effect. Note that materials other than plastic may be used as long as they achieve the desired wave slowing effect. Alternatively, a material with distributed structures may be used as dielectric layer 1305, such as periodic sub-wavelength metallic structures that can be machined or lithographically defined, for example.

An RF array 1306 is on top of dielectric layer 1305. In one embodiment, the distance between interstitial conductor 1303 and RF array 1306 is 0.1-0.15". In another embodiment, this distance may be $\lambda_{eff}/2$, where $\lambda_{eff}$ is the effective wavelength in the medium at the design frequency.

The antenna includes sides 1307 and 1308. Sides 1307 and 1308 are angled to cause a travelling wave feed from coax pin 1301 to be propagated from the area below interstitial conductor 1303 (the spacer layer) to the area above interstitial conductor 1303 (the dielectric layer) via reflection. In one embodiment, the angle of sides 1307 and 1308 are at 45° angles. In an alternative embodiment, sides 1307 and 1308 could be replaced with a continuous radius to achieve the reflection. While FIG. 13B shows angled sides that have angle of 45 degrees, other angles that accomplish signal transmission from lower-level feed to upper-level feed may be used. That is, given that the effective wavelength in the lower feed will generally be different than in the upper feed, some deviation from the ideal 45° angles could be used to aid transmission from the lower to the upper feed level. For example, in another embodiment, the 45° angles are replaced with a single step. The steps on one end of the antenna go around the dielectric layer, interstitial the conductor, and the spacer layer. The same two steps are at the other ends of these layers.

In operation, when a feed wave is fed in from coaxial pin 1301, the wave travels outward concentrically oriented from coaxial pin 1301 in the area between ground plane 1302 and interstitial conductor 1303. The concentrically outgoing waves are reflected by sides 1307 and 1308 and travel inwardly in the area between interstitial conductor 1303 and RF array 1306. The reflection from the edge of the circular perimeter causes the wave to remain in phase (i.e., it is an in-phase reflection). The travelling wave is slowed by dielectric layer 1305. At this point, the travelling wave starts interacting and exciting with elements in RF array 1306 to obtain the desired scattering.

To terminate the travelling wave, a termination 1309 is included in the antenna at the geometric center of the antenna. In one embodiment, termination 1309 comprises a pin termination (e.g., a 50Ω pin). In another embodiment, termination 1309 comprises an RF absorber that terminates unused energy to prevent reflections of that unused energy back through the feed structure of the antenna. These could be used at the top of RF array 1306.

Figure 14:
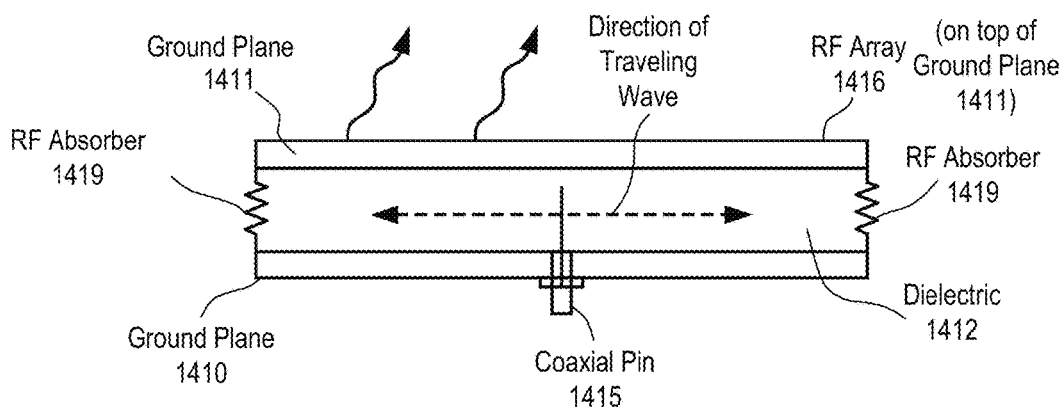
FIG. 14 illustrates another embodiment of the antenna system with an outgoing wave.

FIG. 14 illustrates another embodiment of the antenna system with an outgoing wave. Referring to FIG. 14, two ground planes 1410 and 1411 are substantially parallel to each other with a dielectric layer 1412 (e.g., a plastic layer, etc.) in between ground planes 1410, 1411. RF absorbers 1419 (e.g., resistors) couple the two ground planes 1410 and 1411 together. A coaxial pin 1415 (e.g., 50Ω) feeds the antenna. An RF array 1416 is on top of dielectric layer 1412 and ground plane 1411.

In operation, a feed wave is fed through coaxial pin 1415 and travels concentrically outward and interacts with the elements of RF array 1416.

The cylindrical feed in both the antennas of FIGS. 13B and 14 improves the service angle of the antenna. Instead of a service angle of plus or minus forty-five degrees azimuth (±45° Az) and plus or minus twenty-five degrees elevation (±25° El), in one embodiment, the antenna system has a service angle of seventy-five degrees (75°) from the bore sight in all directions. As with any beam forming antenna comprised of many individual radiators, the overall antenna gain is dependent on the gain of the constituent elements, which themselves are angle-dependent. When using common radiating elements, the overall antenna gain typically decreases as the beam is pointed further off bore sight. At 75 degrees off bore sight, significant gain degradation of about 6 dB is expected.

Embodiments of the antenna having a cylindrical feed solve one or more problems. These include dramatically simplifying the feed structure compared to antennas fed with a corporate divider network and therefore reducing total required antenna and antenna feed volume; decreasing sensitivity to manufacturing and control errors by maintaining high beam performance with coarser controls (extending all the way to simple binary control); giving a more advantageous side lobe pattern compared to rectilinear feeds because the cylindrically oriented feed waves result in spatially diverse side lobes in the far field; and allowing polarization to be dynamic, including allowing left-hand circular, right-hand circular, and linear polarizations, while not requiring a polarizer.

Array of Wave Scattering Elements

RF array 1306 of FIG. 13B and RF array 1416 of FIG. 14 include a wave scattering subsystem that includes a group of patch antennas (e.g., scatterers) that act as radiators. This group of patch antennas comprises an array of scattering metamaterial elements.

In one embodiment, the cylindrical feed geometry of this antenna system allows the unit cells elements to be positioned at forty-five-degree (45°) angles to the vector of the wave in the wave feed. This position of the elements enables control of the polarization of the free space wave generated from or received by the elements. In one embodiment, the unit cells are arranged with an inter-element spacing that is less than a free-space wavelength of the operating frequency of the antenna. For example, if there are four scattering elements per wavelength, the elements in the 30 GHz transmit antenna will be approximately 2.5 mm (i.e., ¼th the 10 mm free-space wavelength of 30 GHz).

Cell Placement

Figure 15:
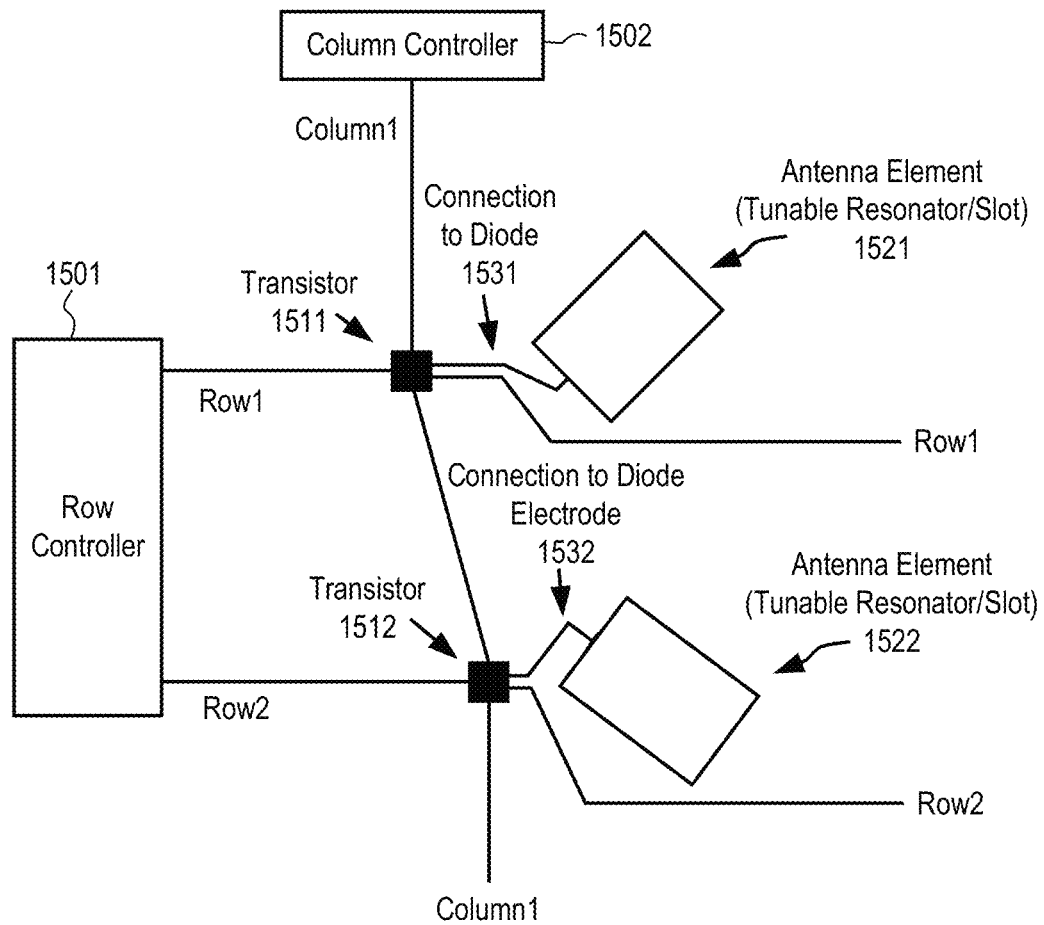
FIG. 15 illustrates one embodiment of the placement of matrix drive circuitry with respect to antenna elements.

In one embodiment, the antenna elements are placed on the cylindrical feed antenna aperture in a way that allows for a systematic matrix drive circuit. The placement of the cells includes placement of the transistors for the matrix drive. FIG. 15 illustrates one embodiment of the placement of matrix drive circuitry with respect to antenna elements. Referring to FIG. 15, row controller 1501 is coupled to transistors 1511 and 1512, via row select signals Row1 and Row2, respectively, and column controller 1502 is coupled to transistors 1511 and 1512 via column select signal Column1. Transistor 1511 is also coupled to antenna element 1521 via connection to diode 1531, while transistor 1512 is coupled to antenna element 1522 via connection to diode 1532.

In an initial approach to realize matrix drive circuitry on the cylindrical feed antenna with unit cells placed in a non-regular grid, two steps are performed. In the first step, the cells are placed on concentric rings and each of the cells is connected to a transistor that is placed beside the cell and acts as a switch to drive each cell separately. In the second step, the matrix drive circuitry is built in order to connect every transistor with a unique address as the matrix drive approach requires. Because the matrix drive circuit is built by row and column traces (similar to LCDs) but the cells are placed on rings, there is no systematic way to assign a unique address to each transistor. This mapping problem results in very complex circuitry to cover all the transistors and leads to a significant increase in the number of physical traces to accomplish the routing. Because of the high density of cells, those traces disturb the RF performance of the antenna due to coupling effect. Also, due to the complexity of traces and high packing density, the routing of the traces cannot be accomplished by commercially available layout tools.

In one embodiment, the matrix drive circuitry is pre-defined before the cells and transistors are placed. This ensures a minimum number of traces that are necessary to drive all the cells, each with a unique address. This strategy reduces the complexity of the drive circuitry and simplifies the routing, which subsequently improves the RF performance of the antenna.

More specifically, in one approach, in the first step, the cells are placed on a regular rectangular grid composed of rows and columns that describe the unique address of each cell. In the second step, the cells are grouped and transformed to concentric circles while maintaining their address and connection to the rows and columns as defined in the first step. A goal of this transformation is not only to put the cells on rings but also to keep the distance between cells and the distance between rings constant over the entire aperture. In order to accomplish this goal, there are several ways to group the cells.

Figure 16:
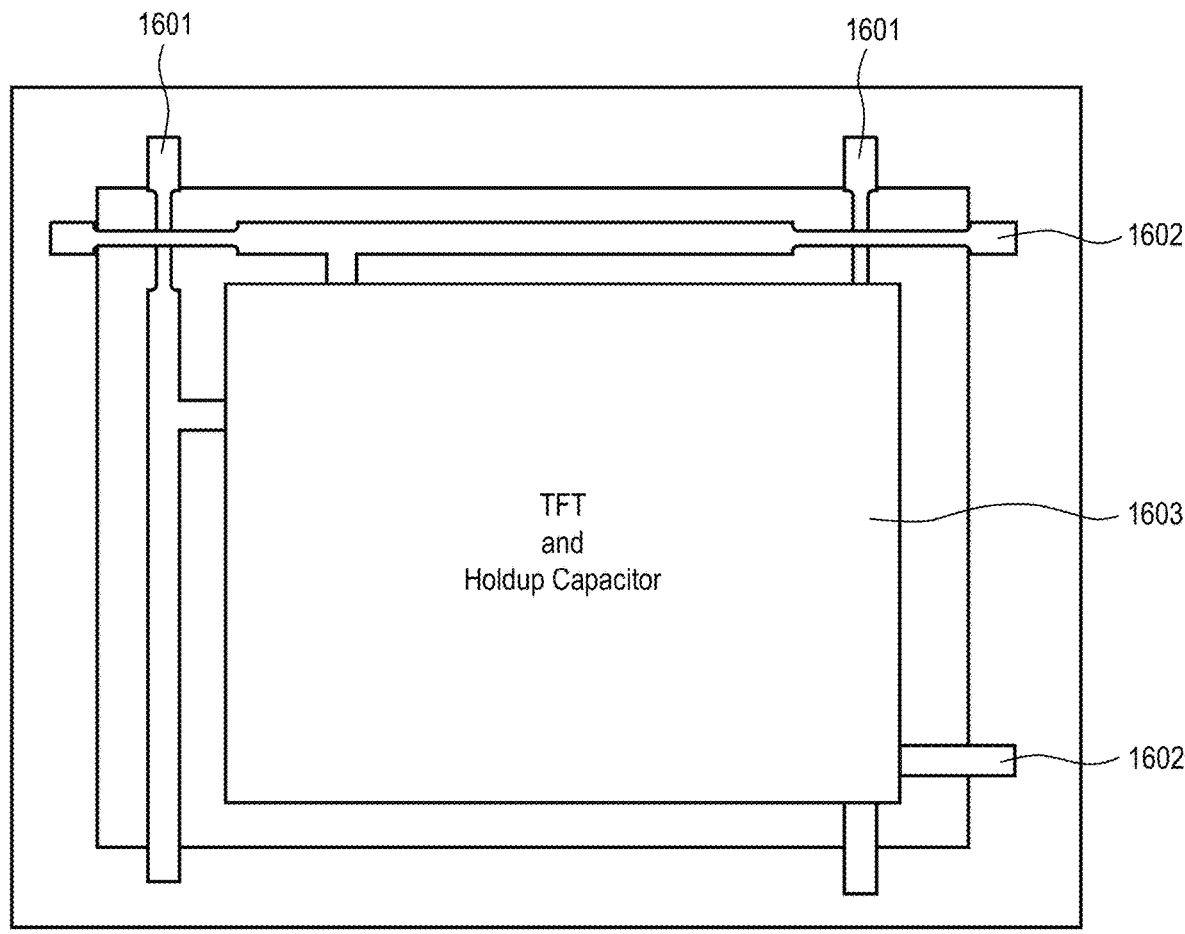
FIG. 16 illustrates one embodiment of a TFT package.

In one embodiment, a TFT package is used to enable placement and unique addressing in the matrix drive. FIG. 16 illustrates one embodiment of a TFT package. Referring to FIG. 16, a TFT and a hold capacitor 1603 is shown with input and output ports. There are two input ports connected to traces 1601 and two output ports connected to traces 1602 to connect the TFTs together using the rows and columns. In one embodiment, the row and column traces cross in 90° angles to reduce, and potentially minimize, the coupling between the row and column traces. In one embodiment, the row and column traces are on different layers.

An Example of a Full Duplex Communication System

Figure 17:
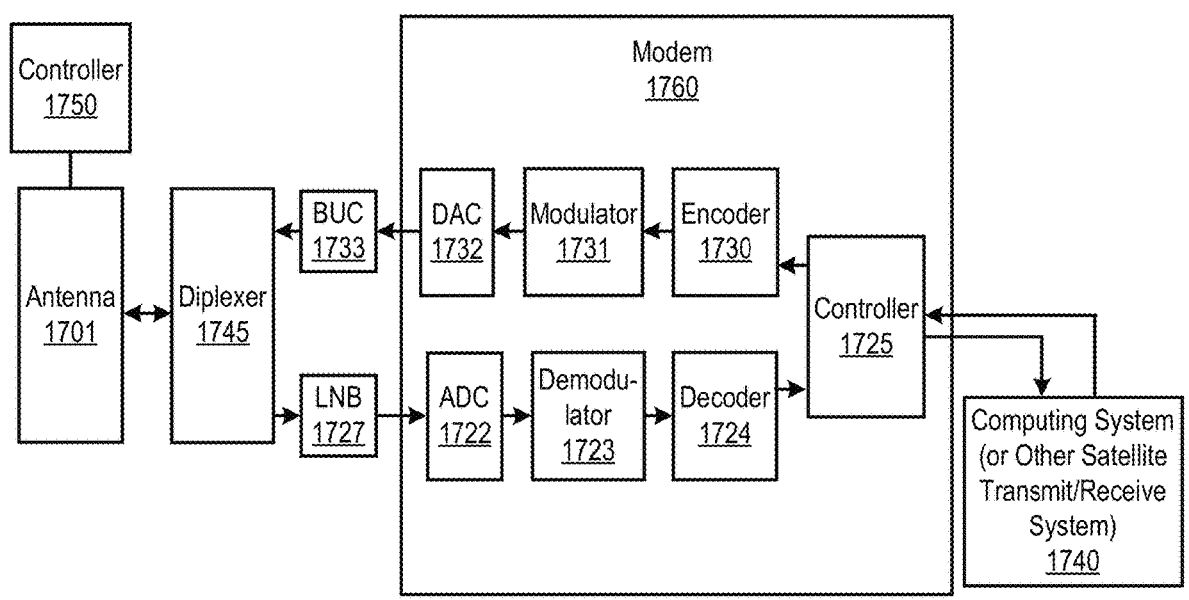
FIG. 17 is a block diagram of one embodiment of a communication system having simultaneous transmit and receive paths.

In another embodiment, the combined antenna apertures are used in a full duplex communication system. FIG. 17 is a block diagram of an embodiment of a communication system having simultaneous transmit and receive paths. While only one transmit path and one receive path are shown, the communication system may include more than one transmit path and/or more than one receive path.

Referring to FIG. 17, antenna 1701 includes two spatially interleaved antenna arrays operable independently to transmit and receive simultaneously at different frequencies as described above. In one embodiment, antenna 1701 is coupled to diplexer 1745. The coupling may be by one or more feeding networks. In one embodiment, in the case of a radial feed antenna, diplexer 1745 combines the two signals and the connection between antenna 1701 and diplexer 1745 is a single broad-band feeding network that can carry both frequencies.

Diplexer 1745 is coupled to a low noise block down converter (LNBs) 1727, which performs a noise filtering function and a down conversion and amplification function in a manner well-known in the art. In one embodiment, LNB 1727 is in an out-door unit (ODU). In another embodiment, LNB 1727 is integrated into the antenna apparatus. LNB 1727 is coupled to a modem 1760, which is coupled to computing system 1740 (e.g., a computer system, modem, etc.).

Modem 1760 includes an analog-to-digital converter (ADC) 1722, which is coupled to LNB 1727, to convert the received signal output from diplexer 1745 into digital format. Once converted to digital format, the signal is demodulated by demodulator 1723 and decoded by decoder 1724 to obtain the encoded data on the received wave. The decoded data is then sent to controller 1725, which sends it to computing system 1740.

Modem 1760 also includes an encoder 1730 that encodes data to be transmitted from computing system 1740. The encoded data is modulated by modulator 1731 and then converted to analog by digital-to-analog converter (DAC) 1732. The analog signal is then filtered by a BUC (up-convert and high pass amplifier) 1733 and provided to one port of diplexer 1745. In one embodiment, BUC 1733 is in an out-door unit (ODU).

Diplexer 1745 operating in a manner well-known in the art provides the transmit signal to antenna 1701 for transmission.

Controller 1750 controls antenna 1701, including the two arrays of antenna elements on the single combined physical aperture.

The communication system would be modified to include the combiner/arbiter described above. In such a case, the combiner/arbiter after the modem but before the BUC and LNB.

Note that the full duplex communication system shown in FIG. 17 has a number of applications, including but not limited to, internet communication, vehicle communication (including software updating), etc.

With reference to FIGS. 1-17, it should be appreciated that other tunable capacitors, tunable capacitance dies, packaged dies, micro-electromechanical systems (MEMS) devices, or other tunable capacitance devices, could be placed into an aperture or elsewhere in variations on the embodiments described herein, for further embodiments. The techniques for mass transfer may be applicable to further embodiments, including placement of various dies, packaged dies or MEMS devices on various substrates for electronically scanned arrays and various further electrical, electronic and electromechanical devices.

There is a number of example embodiments described herein.

Example 1 is an antenna comprising: an array of antenna elements, wherein each antenna element comprises a iris and a varactor diode integrated on an integrated circuit (IC) chip coupled across a portion of the iris; and a plurality of transistors, each transistor coupled to a distinct one of the varactor diodes in the array of antenna elements to provide a tuning voltage to the one varactor diode.

Example 2 is the antenna of example 1 that may optionally include that the diode comprises a single junction varactor diode.

Example 3 is the antenna of example 1 that may optionally include that the diode comprises a dual junction varactor diode.

Example 4 is the antenna of example 3 that may optionally include that the dual junction varactor diode comprises two junction capacitors in series.

Example 5 is the antenna of example 1 that may optionally include that each antenna element comprises a capacitor coupled in series with the diode.

Example 6 is the antenna of example 1 that may optionally include that the capacitor is part of the IC chip.

Example 7 is the antenna of example 1 that may optionally include that each transistor is part of the IC chip with the one varactor diode.

Example 8 is the antenna of example 1 that may optionally include that the IC chip further comprises an amplifier coupled to the varactor diode to amplify a radio-frequency (RF) current across the IC.

Example 9 is the antenna of example 1 that may optionally include that the IC chip further comprises a sensor to monitor voltage at the varactor diode.

Example 10 is the antenna of example 9 that may optionally include that the sensor comprises a voltage sampling circuit.

Example 11 is the antenna of example 1 that may optionally include that the plurality of transistors are part of a matrix drive.

Example 12 is the antenna of example 1 that may optionally include that the plurality of transistors are part of direct drive.

Example 13 is an antenna comprising: an antenna aperture having a plurality of irises; a plurality of integrated circuit (IC) chips coupled to the plurality of irises, each IC having a varactor diode coupled across a portion of a iris of the plurality of irises and is coupled between radio-frequency (RF) terminals, wherein said each IC further comprises a transistor coupled to provide a tuning voltage to the varactor diode, and an amplifier coupled to the varactor diode to amplify an RF signal propagating across the RF terminals and through the IC.

Example 14 is the antenna of example 13 that may optionally include that the diode comprises a single junction varactor diode.

Example 15 is the antenna of example 13 that may optionally include that the IC chip further comprises a sensor.

Example 16 is the antenna of example 15 that may optionally include that the sensor is to monitor voltage at the varactor diode.

Example 17 is the antenna of example 15 that may optionally include that the sensor comprises a voltage sampling circuit.

Example 18 is an antenna comprising: an antenna aperture having a plurality of irises; a plurality of integrated circuit (IC) chips coupled to the plurality of irises, each IC having a dual junction varactor diode coupled across a portion of a iris of the plurality of irises and coupled between RF terminals; and a plurality of transistors, each transistor coupled to a distinct one of the dual junction varactor diodes to provide a tuning voltage to the one dual junction varactor diode.

Example 19 is the antenna of example 18 that may optionally include that the dual junction varactor diode comprises two junction capacitors coupled in series at a junction and said each transistor is configured to provide the tuning voltage to the junction.

Example 20 is the antenna of example 18 that may optionally include that each of the plurality of ICs further comprises one of the plurality of transistors.

Example 21 is the antenna of example 18 that may optionally include that the dual junction varactor diode has a common cathode.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. An antenna comprising:
an array of antenna elements, wherein each antenna element comprises an iris and a varactor diode integrated on an integrated circuit (IC) chip coupled across a portion of the iris, the varactor diode to operate as a tuning element for said each antenna element, wherein the iris has an elongated shape having first and second edges on opposite ends of the elongated shape;
a plurality of transistors, each transistor coupled to a distinct one of the varactor diodes in the array of antenna elements for providing a tuning voltage to the one varactor diode, wherein each of the plurality of transistors is part of matrix drive for supplying a drive voltage to control the varactor diode in the IC chip coupled across the portion of the iris of one of the antenna elements,
a plurality of bias lines coupled to the plurality of transistors and for supplying a direct current (DC) bias voltage for the varactor diode, with each bias line being coupled to a transistor of the plurality of transistors and being routed in a direction that crosses the first edge and proceeds to the IC chip coupled across the portion of the iris; and
a plurality of isolation devices coupled to the plurality of bias lines, with each isolation device of the isolation devices to isolate a radio frequency (RF) signal of the iris of one antenna element of the plurality of antenna elements from the DC bias voltage for the varactor diode of the one antenna element.

2. The antenna of claim 1 wherein the diode comprises a single junction varactor diode.

3. The antenna of claim 1 wherein the diode comprises a dual junction varactor diode.

4. The antenna of claim 3 wherein the dual junction varactor diode comprises two junction capacitors in series.

5. The antenna of claim 1 wherein each antenna element comprises a capacitor coupled in series with the diode.

6. The antenna of claim 1 wherein the capacitor is part of the IC chip.

7. The antenna of claim 1 wherein said each transistor is part of the IC chip with the one varactor diode.

8. The antenna of claim 1 wherein each of the irises of the antenna elements are around on its sides by an iris metal layer.

9. An antenna comprising:
an array of antenna elements, wherein each antenna element comprises an iris and a varactor diode integrated on an integrated circuit (IC) chip coupled across a portion of the iris, wherein the IC chip further comprises an amplifier coupled to the varactor diode to amplify a radio-frequency (RF) current across the IC; and
a plurality of transistors, each transistor coupled to a distinct one of the varactor diodes in the array of antenna elements to provide a tuning voltage to the one varactor diode.

10. An antenna comprising:
an array of antenna elements, wherein each antenna element comprises an iris and a varactor diode integrated on an integrated circuit (IC) chip coupled across a portion of the iris, wherein the IC chip further comprises a sensor to monitor voltage at the varactor diode; and a plurality of transistors, each transistor coupled to a distinct one of the varactor diodes in the array of antenna elements to provide a tuning voltage to the one varactor diode.

11. The antenna of claim 10 wherein the sensor comprises a voltage sampling circuit.

12. An antenna comprising:
an antenna aperture having a plurality of irises;
a plurality of integrated circuit (IC) chips coupled to the plurality of irises, each IC having a varactor diode coupled across a portion of an iris of the plurality of irises and is coupled between radio-frequency (RF) terminals,
wherein said each IC further comprises
a transistor coupled to provide a tuning voltage to the varactor diode, and
an amplifier coupled to the varactor diode to amplify an RF signal propagating across the RF terminals and through the IC.

13. The antenna of claim 12 wherein the diode comprises a single junction varactor diode.

14. The antenna of claim 12 wherein the IC chip further comprises a sensor.

15. The antenna of claim 14 wherein the sensor is to monitor voltage at the varactor diode.

16. The antenna of claim 14 wherein the sensor comprises a voltage sampling circuit.

17. An antenna comprising:
an antenna aperture having a plurality of irises;
a plurality of integrated circuit (IC) chips coupled to the plurality of irises, each IC having a dual junction varactor diode coupled across a portion of an iris of the plurality of irises and coupled between RF terminals, the dual junction varactor diode to operate as a tuning element for said each antenna element, wherein the iris has an elongated shape having first and second edges on opposite ends of the elongated shape;
a plurality of transistors, each transistor coupled to a distinct one of the dual junction varactor diodes to provide a tuning voltage to the one dual junction varactor diode, wherein each of the plurality of transistors is part of matrix drive for supplying a drive voltage to control the varactor diode in the IC chip coupled across the iris of one of the antenna elements, and
a plurality of bias lines coupled to the plurality of transistors and for supplying a direct current (DC) bias voltage for the dual junction varactor diode, with each bias line being coupled to a transistor of the plurality of transistors and being routed in a direction that crosses the first edge and proceeds to the IC chip coupled across the portion of the iris; and
a plurality of isolation devices coupled to the plurality of bias lines, with each isolation device of the isolation devices to isolate a radio frequency (RF) signal of the iris of one antenna element of the plurality of antenna elements from the DC bias voltage for the dual junction varactor diode of the one antenna element.

18. The antenna of claim 17 wherein the dual junction varactor diode comprises two junction capacitors coupled in series at a junction and said each transistor is configured to provide the tuning voltage to the junction.

19. The antenna of claim 17 wherein each of the plurality of ICs further comprises one of the plurality of transistors.

20. The antenna of claim 17 wherein the dual junction varactor diode has a common cathode.

* * * * *